United States Patent [19]

Beisswenger et al.

[11] Patent Number: 5,455,264
[45] Date of Patent: Oct. 3, 1995

[54] RS-THIOCTIC ACID WITH NOVEL MORPHOLOGY

[75] Inventors: Thomas Beisswenger, Bad Vilbelel; Horst Bethge; Joachim Goede, both of Hanau; Frank Hübner, Ober-Ramstadt; Klaus Huthmacher, Gelnhausen; Herbert Klenk, Hanau; Roland Möller, Hammersbach, all of Germany

[73] Assignee: ASTA Medica Aktiengesellschaft, Dresden, Germany

[21] Appl. No.: 134,695

[22] Filed: Oct. 12, 1993

[30] Foreign Application Priority Data

Oct. 23, 1992 [DE] Germany .................. 42 35 912.0

[51] Int. Cl.⁶ .................. A61K 31/385; C07D 339/04
[52] U.S. Cl. .................. 514/440; 549/39
[58] Field of Search .................. 549/39; 514/440

[56] References Cited

U.S. PATENT DOCUMENTS 2,933,430  4/1960  Rosenberg .................. 514/440
3,049,549  8/1962  Reed et al. .................. 549/39
4,772,727  9/1988  Sutherland et al. .................. 549/39

OTHER PUBLICATIONS

"The Merck Index", 9th Ed, Merck & Co., Inc., 1976, pp. 1203–1204.

Brookes et al, "Proof that the Absolute Configuration of Natural α–Lipoic Acid is R by the Synthesis of its Enantiomer [(S)–(–)–α–Lipoic Acid] from (S)–Malic Acid," JCS, Chem Comm, p. 1051 (1988).

Reed et al II, "Isolation, Characterization & Structure of α–Lipoic Acid," J. Am. Chem. Soc., vol. 75, No. 6, p. 1267 (1953).

Primary Examiner—Glennon H. Hollrah
Assistant Examiner—Mary C. Cebulak
Attorney, Agent, or Firm—Cushman Darby & Cushman

[57] ABSTRACT

RS-thioctic acid with a novel morphology which is obtained by a recrystallization process.

6 Claims, 4 Drawing Sheets

RS-THIOCTIC ACID WITH NOVEL MORPHOLOGY

The present invention relates to a novel form of thioctic acid and to a method of making it by recrystallization.

BACKGROUND OF THE INVENTION

RS-thioctic acid (DL-alpha-lipoic acid) is used in pharmaceutical formulations both in infusion solutions and also in solid galenic forms for oral administration. All references hereinbelow to thioctic acid relate both to the enantiomerically pure compounds (R- or S-thioctic acid) and also to the racemic mixture (R,S-thioctic acid) and mixtures with any proportions of enantiomers.

Synthetically obtained DL-thioctic acid which is used for this purpose is obtained via the first step of dihydrolipoic acid (6,8-dimercaptooctanic acid) by means of oxidation. The synthetic process may also be carried out by producing enantiomerically pure R- or S-thioctic acid from enantiomerically pure R- or S-dihydrolipoic acid and advantageously using this (D- or L-alpha-lipoic acid) DE 41 37 773.7, EP 0427247 (U.S. Application of Blaschke, Ser. No. 07/975,075, filed Nov. 12, 1992). Enantiomerically pure R-thioctic acid and S-thioctic acid is, however, also obtainable using the process described in German published patent 36 29 116 (U.S. Pat. No. 4,772,727).

The material hitherto available has not had a very favorable form for pharmaceutical processing; it was not free-flowing, leading to irregularities during filling and necessitating an increased use of auxiliary substances or an intensive granulation in order to produce pharmaceutical tablets. In addition, it tends to create dust which is a disadvantage from the point of view of safety provisions.

Processes are known from the literature for the preparation of pure, pharmaceutically useful, thioctic acid in a form favorable for galenic processing (Chem. Ber. 1959, 1177) in which the dimercaptooctanic acid is distilled and again purified by distillation after oxidation to thioctic acid in order to be finally obtained at −70° C. in crystalline form from ethyl acetate. Another method (J.Am.Chem.Soc. 77(1955), 416) uses the viscous oil obtained after oxidation of dimercaptooctanic acid by concentration of the organic solvents. This is extracted several times with Skellysolve B, a fluctuating proportion of a "polymeric" material remaining.

The combined extracts are inoculated and crystallized at room temperature or for a few hours in a refrigerator. The recrystallization from Skellysolve B finally yields an analytically pure material with a melting point of 61° C.– 62° C.

Another specification (J.Am.Chem.Soc. 77(1955) 5148) recommends cyclohexane for the extraction and crystallization, enantiomerically pure (+)-alpha-lipoic acid also being obtained in analogous manner (J. Chem. Soc. Perkin Trans. 1(1990), 1615). Crystallizates obtained in this manner display the X-ray diffractograms published by Reed et al., J.Am.Chem.Soc., 7(1953)1267 for (+)-alpha-lipoic acid and those published by Eli Lilly for DL-alpha-lipoic acid. [Transmission-X-ray diffractometer photos with Cu $K_{\alpha 1}$-radiation (2 theta)].

SUMMARY OF THE INVENTION

It is an object of the present invention to provide a process for the preparation of pure, pharmaceutically useful thioctic acid in a form favorable for galenic processing.

These and other objects are achieved by transferring the sodium salt of alpha-lipoic acid, formed by oxidation of the 6,8-dimercaptooctanic acid sodium salt in aqueous solution, into the free alpha-lipoic acid by adding mineral salts, and then extracting directly into an organic solvent with a dielectric constant epsilon of 2.5 to 5.5 at room temperature. The organic alpha-lipoic acid solution formed is then slowly cooled to +10° C. to −20° C. after complete phase separation. A novel crystallizate is formed, both for racemically and also for enantiomerically pure alpha-lipoic acid, which has an X-ray diffraction pattern with a novel line intensity distribution and a particle size distribution and particle characteristics suitable for processing. In addition, the material of the invention has a higher dissolution speed in aqueous phosphate buffer (pH 6.8) compared to commercial material, and fewer lumps are formed.

The novel product is characterized as follows;

a) the intensity ratio of the reflection lines at 20°=18° and 20°=22° is at least 1 for RS-thioctic acid and the intensity ratio of the reflection lines at 20°=18° and 20°=22° is at least 2.5 for R- or S-thioctic acid.

b) In aqueous solution the material of the invention has an extinction of <0.300 (430 nm) (1 g thioctic acid in 20 ml 1N NaOH), layer thickness 1 cm.

The use of the solvents of the invention with a dielectric constant of 2.5 to 5.5 also has the advantage over the solvents described in the literature in that they produce a very pure crystallizate on crystallization whereas, for example, precipitation from cyclohexane leads to the inclusion of secondary compounds. Solvents that may for example be used are: aliphatic hydrocarbons with a chain length of $C_5$–$C_7$, cycloaliphatic hydrocarbons such as cyclopentane, cyclohexane, methylcyclohexane carboxylic acid esters of aliphatic carboxylic acids such as acetic acid and propionic acid with aliphatic alcohols such as methanol, ethanol or propanol as well as ethers of aliphatic alcohols with a chain length of 1–4 carbon atoms. The ethers may also be closed-ring, such as for example tetrahydrofuran or dioxane. It is also possible to use mixtures of the solvents described above, provided always that the solvent mixture has the required dielectric constant.

By-products formed during the synthesis of thioctic acid are for example 6-mercapto-8-chlorooctanic acid or 6-chloro-8-mercaptooctanic acid which form polymeric disulfides after oxidation of the substance mixture with 6,8-dimercaptooctanic acid. To permit pharmaceutical administration the disulfides must be separated with the mother liquor.

The object of the invention, namely the removal of by-products occurring during the synthesis without distillation of the 6,8-dimercaptooctanic acid or the thioctic acid itself can thus be simply achieved and without the decomposition of the octanic acids which would otherwise be expected.

The product of the invention also dissolves more quickly than material produced by known methods, and it does not form any agglomerates.

DETAILED DESCRIPTION OF PREFERRED EMBODIMENTS

The invention is illustrated by the following examples.

Example 1

Amounts used:
50.0 g R(+)-alpha-lipoic acid
500 ml mixture of cyclohexane/ethyl acetate 2:1
Method:

50 g R(+)-alpha-lipoic acid were added to 500 ml of the above-mentioned solvent mixture at room temperature. The temperature fell to 10° C. and a clear solution was obtained after a few minutes. Small amounts of polymer portions remained in undissolved form.

The solvent was decanted off and slowly cooled with stirring with ice water. The ice/sodium chloride solution was then slowly further cooled.

The crystallization process began at −6° C. After the main amount had crystallized out, cooling was continued to about −15° C. and stirring continued for 2 hours at this temperature.

The resulting product was then suctioned off and dried in a vacuum at room temperature.

Result:
  15.6 g R(+)-alpha-lipoic acid
  Yield: 31%

The mother liquor may be used for further crystallizations.

Example 2

Recrystallization of RS-alpha-lipoic acid from diisopropyl ether

Amounts used:
  50.0 g RS-alpha-lipoic acid
  500 ml diisopropyl ether

Method:

50 g RS-alpha-lipoic acid were added to 500 ml diisopropyl ether at room temperature. The mixture was heated slowly with hot water. A clear solution was obtained at 33° C. Small amounts of polymer portions remained undissolved.

The solution was filtered off at 33° C. and slowly cooled while stirring with ice water.

The crystallization process began at 15°–16° C. When the main amount had crystallized out, cooling continued slowly down to about −15° C. with ice/sodium chloride mixture and stirring continued for 2 hours at this temperature.

The resulting product was then suctioned off and dried in a vacuum at room temperature.

Result:
  38.2 g RS-alpha-lipoic acid
  Yield: 76%

Example 3

Recrystallization of RS-alpha-lipoic acid from pentane/ethyl acetate 2:1

Amounts used:
  50.0 g R,S-alpha-lipoic acid
  500 ml mixture of pentane/ethyl acetate 2:1

Method:

50 g RS-alpha-lipoic acid were added to 500 ml of the above solvent mixture at room temperature.

The mixture was slowly heated with hot water.

A clear solution was obtained at 35° C. Small amounts of polymer portions remained undissolved.

The solution was filtered off at 35° C. and slowly cooled with stirring with ice water.

The crystallization process began at 16°–17° C. When the main amount had crystallized out, cooling continued slowly down to about −15° C. with ice/sodium chloride mixture and stirring continued for 2 hours at this temperature.

The resulting product was then suctioned off and dried in a vacuum at room temperature.

Result:
  40.4 g RS-alpha-lipoic acid
  Yield: 81%

Example 4

Recrystallization of RS-alpha-lipoic acid from cyclohexane/ethyl acetate 5:1

Amounts used:
  50.0 g R,S-alpha-lipoic acid
  500 ml mixture of cyclohexane/ethyl acetate 5:1

Method:

50 g RS-alpha-lipoic acid were added to 500 ml solvent mixture at room temperature.

The mixture was slowly heated with hot water. A clear solution was obtained at 41° C. Small amounts of polymer portions remained undissolved.

The solution was filtered off at 40° C. and slowly cooled with stirring.

The crystallization process began at 26°–27° C. When the main amount had crystallized out, cooling continued slowly down to about 5° C. with ice water and stirring continued for 2 hours at this temperature.

The resulting product was then suctioned off and dried in a vacuum at room temperature.

Result:
  44.4 g RS-alpha-lipoic acid
  Yield: 89%

The thioctic acids prepared according to the invention were subjected to an X-ray diffraction analysis with Cu K-alpha radiation.

BRIEF DESCRIPTION OF FIGURES OF DRAWING

In the drawings:

FIG. 1 shows the X-ray diffraction powder diagram of the raw material (racemic mixture);

FIG. 2 shows the X-ray diffraction powder diagram of the material of the invention (racemic mixture);

Figure 1:
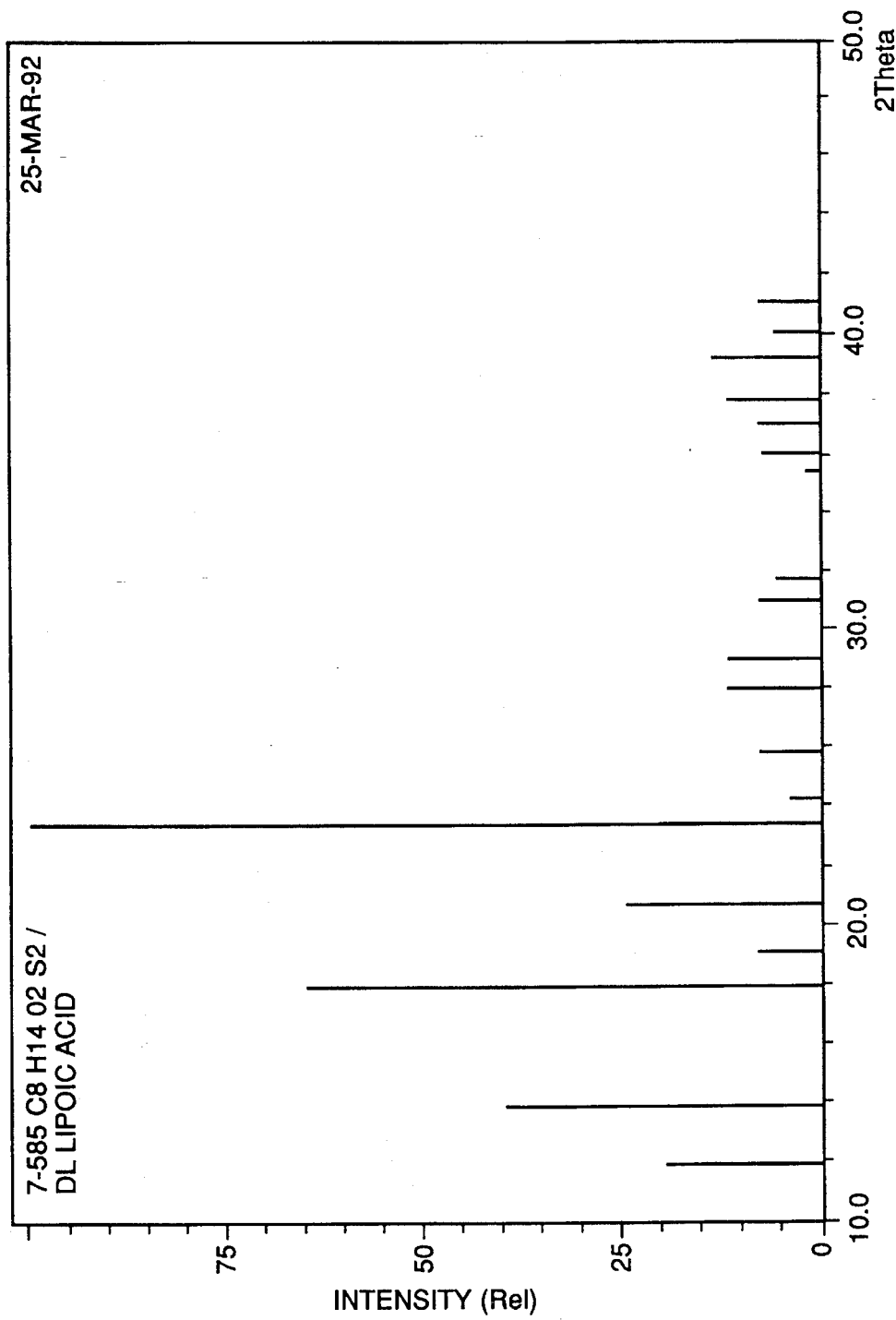
FIG. 1 shows an RS-thioctic acid according to the state of the art and, more specifically.
Figure 2:
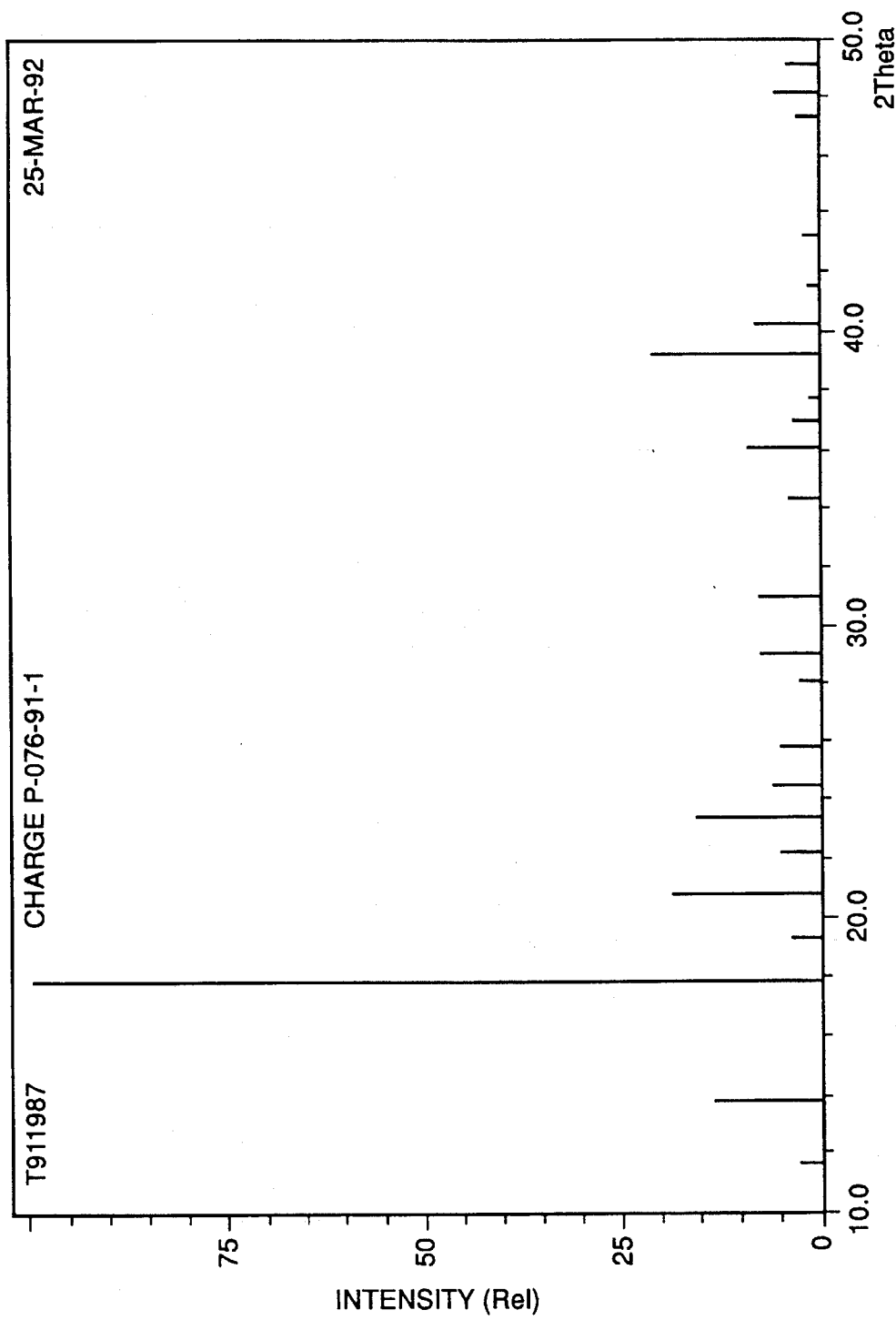
FIG. 2 shows the analysis of the RS-thioctic acid of the invention and more specifically.
Figure 3:
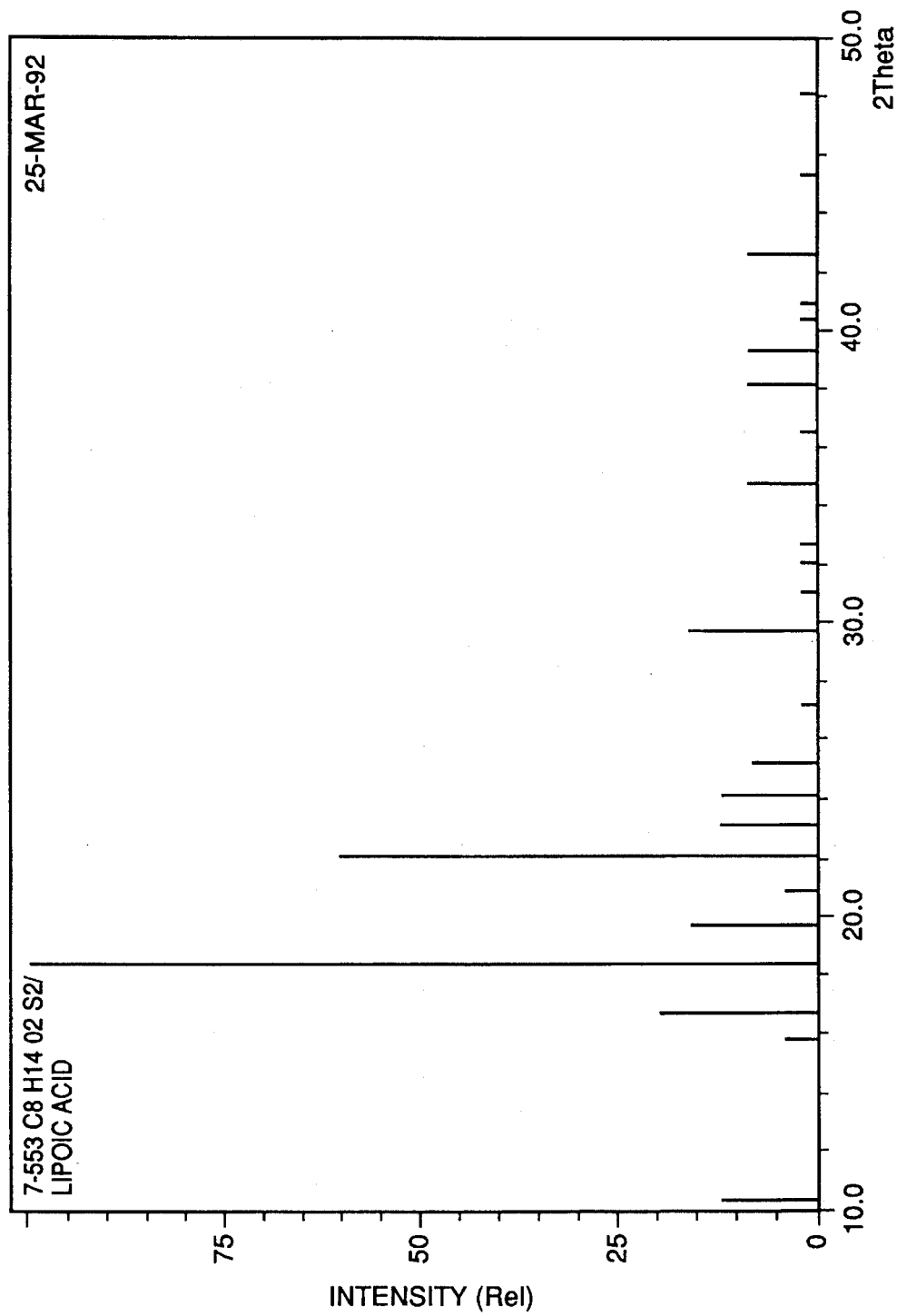
Figure 4:
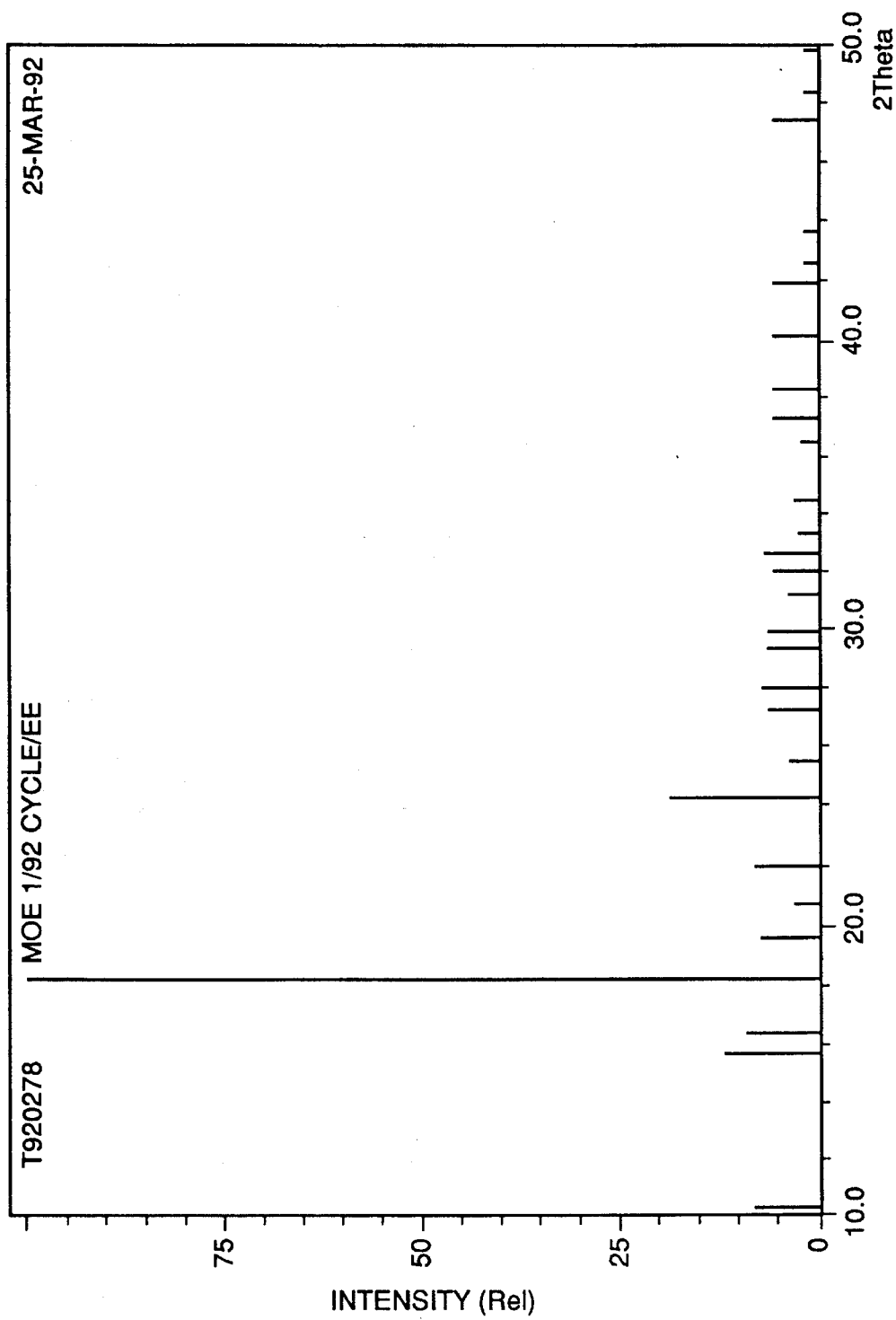

FIG. 3 shows an R-thioctoic acid according to the state of the art, and more specifically, FIG. 3 shows the X-ray diffraction powder diagram of a conventional, enantiomerically pure R-alpha-lipoic acid; and FIG. 4 shows an analysis of the R-thioctic acid of the invention, and, more specifically, FIG. 4 shows the X-ray diffraction powder diagram of an enantiomerically pure R-alpha-lipoic acid of the invention.

What is claimed is:

1. A compound selected from the group consisting of crystalline RS-thioctic acid, R(+)-thioctic acid and S(−)-thioctic acid, characterized by the following properties:

a) the intensity ratio of the reflection lines at $2\theta°=18°$ and $2\theta°=22°$ is at least 1 for RS-thioctic acid and the intensity ratio of the reflection lines at $2\theta°=18°$ $2\theta°=22°$ is at least 2.5 for R- or S-thioctic acid, and of the reflection lines at $2\theta°=18°$ $2\theta°=22°$ is at least 2.5 for R- or S-thioctic acid, and b) the extinction coefficient of a solution of 1 g thioctic acid in 20 ml 1N NaOH is <0.300 (430 nm).

2. A pharmaceutical composition comprising thioctic acid according to claim 1 and a pharmaceutically acceptable carrier thereof.

3. A process for the preparation of crystalline thioctic acid, which comprises dissolving one part of thioctic acid at 10° C. to 60° C. in 5–20 parts solvent or solvent mixture having a dielectric constant epsilon between 2.5 and 5.5, and cooling the solvent or solvent mixture within 2–10 hours to 0° C. to −20° C.

4. A process according to claim 3 in which the solvent contains a mixture of solvents selected from the group consisting of pentane, cyclohexane, acetic acid ethyl ester and ethers.

5. Thioctic acid in the physical form produced by the process of claim 3 or claim 4.

6. A pharmaceutical composition comprising thioctic acid according to claim 5 and a pharmaceutically acceptable carrier therefor.

* * * * *